United States Patent [19]

Krause et al.

[11] 3,956,383

[45] May 11, 1976

[54] METHOD FOR MANUFACTURING ETHER POLYCARBOXYLIC ACIDS

[75] Inventors: Horst-Jürgen Krause; Günther Tischbirek, both of Dusseldorf-Holthausen, Germany

[73] Assignee: Henkel & Cie G.m.b.H., Dusseldorf, Germany

[22] Filed: Oct. 21, 1974

[21] Appl. No.: 516,210

[30] Foreign Application Priority Data

Mar. 4, 1974 Austria .................................. 1759/74

[52] U.S. Cl. ............................ 260/535 P; 260/484 P
[51] Int. Cl.² .......................................... C07C 59/22
[58] Field of Search ...................... 260/535 P, 484 P

[56] References Cited

FOREIGN PATENTS OR APPLICATIONS 902,359  8/1962  United Kingdom ............. 260/484 P

*Primary Examiner*—Anton H. Sutto
*Assistant Examiner*—Paul J. Killos
*Attorney, Agent, or Firm*—Hammond & Littell

[57] ABSTRACT

A process for the production of ether polycarboxylic acids comprising reacting alkali metal salts of ether carboxylic acids with carbon dioxide in the presence of (1) an alkali metal alcoholate and (2) optionally, heavy metal catalysts and inert diluents at temperatures of 200°C to 350°C under pressure, acidify the resulting alkali metal salt of an ether polycarboxylic acid and recovering the ether polycarboxylic acid.

10 Claims, No Drawings

METHOD FOR MANUFACTURING ETHER POLYCARBOXYLIC ACIDS

It is known that ether polycarboxylic acids, as well as their alkali salts are good sequestering agents, particularly for the hardness-formers of water. But the practical use of these products was heretofore prevented by the fact that there was no economical production method for them. There is therefore a need for a method which permits the production of these compounds on a large technical scale.

U.S. Pat. No. 3,359,310 describes a method for the production of the potassium salt of malonic acid or malonic acid itself by the carboxylation of potassium acetate with carbon dioxide under pressure in the presence of potasssium carbonate and a heavy metal catalyst at temperatures of about 300°C. However, one skilled in the art would not expect this reaction with its arduous conditions of pressure and temperature to be applied to labile ether carboxylic acids because, according to general knowledge, ethers are very easily cleaved by the action of metals at higher temperatures.

An object of the present invention is the development of a process for the production of ether polycarboxylic acids consisting essentially of reacting an alkali metal salt of an ether carboxylic acid having the formula

R — O — CHR' — COOH wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alcoholate of an alkanol having from 1 to 4 carbon atoms and (2) from 0% to 70% by weight, based on the weight of the reaction mixture of a heavy metal catalyst, an alkanol having from 1 to 4 carbon atoms, a dialkyl carbonate having from 1 to 4 carbon atoms in the alkyl, a finely-divided inert diluent and an inert liquid diluent, at a temperature of between 200°C and 350°C under a pressure of at least 2 atmospheres gauge, for a time sufficient to effect carboxylation, and recovering said ether polycarboxylic acids.

This and other objects of the invention will become more apparent as the description thereof proceeds.

The present invention is directed to a process for preparing ether polycarboxylic acids from the alkali metal salt of ether carboxylic acids in the presence of alkali metal alcoholates by reacting with carbon dioxide at elevated temperatures and pressures.

The above objects were achieved and the problems of the prior art were overcome in that an ether carboxylic acid of the formula

R — O — CHR' — COOH where R denotes an alkyl with 1 to 22 carbon atoms, which can be straight-chain or branch-chain, and substituted by hydroxyl or carboxyl groups or interrupted by oxygen atoms, and where R' denotes hydrogen or a lower alkyl with 1 to 4 carbon atoms, is reacted in the form of its alkali metal salts in the presence of alkali metal alcoholates, and, optionally, heavy metal catalysts, as well as inert diluents, with carbon dioxide at temperatures of 200°C to 350°C, preferably 250°C to 300°C under pressure, preferably above 100 atmospheres gauge, and that the alkali metal salt of the ether polycarboxylic acids formed is transformed, if necessary, in known manner into the free acids to give the desired ether polycarboxylic acids.

More particularly, the invention relates to a process for the production of ether polycarboxylic acids consisting of reacting an alkali metal salt of an ether carboxylic acid having the formula

R — O — CHR' — COOH wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alcoholate of an alkanol having from 1 to 4 carbon atoms and (2) from 0% to 70% by weight, based on the weight of the reaction mixture of a heavy metal catalyst, an alkanol having from 1 to 4 carbon atoms, a dialkyl carbonate having from 1 to 4 carbon atoms in the alkyl, a finely-divided inert diluent and an inert liquid diluent, at a temperature of between 200°C and 350°C under a pressure of at 2 atmospheres gauge, for a time sufficient to effect carboxylation, and recovering said ether polycarboxylic acids.

As indicated above, U.S. Pat. No. 3,359,310 gives a process for the production of potassium malonate or malonic acid by carboxylation of potassium acetate with carbon dioxide under pressure in the presence of potassium carbonate and heavy metal catalysts at temperatures of about 300°C. Application of this reaction with its adverse conditions of pressure and temperature to the labile ether carboxylic acids would seem out of the question for the man skilled in the art since, according to general knowledge, ethers are very easily split during metallization at higher temperatures.

It was completely unexpected, therefore, to find according to the invention that the alkali metal salts of the ethers of α-hydroxycarboxylic acids of the above-mentioned general formula could be carboxylated with a high yield in the presence of alkali metal alcoholates and carbon dioxide under pressure, while maintaining certain temperature conditions. The carboxylation is effected on the carbon atom in the α-position to the carboxyl group. With ether carboxylic acids which contain several carboxyl groups in the molecule, carboxylation is possible on all carbon atoms which are in α-position to carboxyl groups or on only one carbon atom which is in the adjacent or α-position to a carboxyl group. The degree of reaction of the carboxylation depends to a great extent on the selected temperature conditions.

The carboxylation of the ether carboxylic acids to be reacted takes place in the presence of alkali metal alcoholate according to the following reaction:

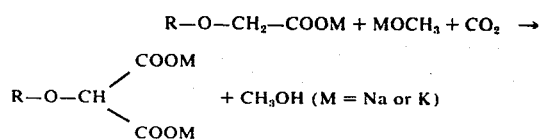

Where a dicarboxylic acid such as diglycolic acid is employed the reaction is as follows:

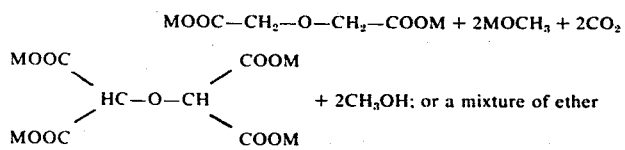

polycarboxylic acids are prepared as follows:

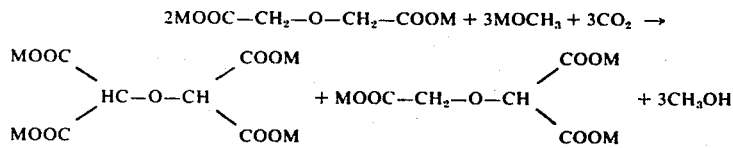

Examples of metal cations of the alkali metal alcoholates are sodium or potassium, preferably sodium.

The alcohol components of the metal alcoholates is an aliphatic alcohol with 1 to 4 carbon atoms, particularly an alkanol of 1 to 4 carbon atoms such as methanol, ethanol, propanol, isopropanol, n-butanol, sec.-butanol, tert.-butanol.

All alkali metal salts of ether carboxylic acids which meet the conditions of the above-mentioned general formula can be used as starting materials for the production of the other polycarboxylic acids according to the invention. Examples of such compounds suitable for carboxylation are the alkali metal salts of alkylglycolic acids such as methylglycolic acid, ethylglycolic acid, butylglycolic acid, laurylglycolic acid, alkyl-$C_{12-18}$- glycolic acid, also oxaalkylglycolic acids or polyoxaalkylglycolic acids such as etherification products of glycolic acids with ethylene-oxide (EO) addition products on alcohols, particularly on fatty alcohols, such as the lauryl alcohol + 2 EO ether of glycolic acid, myristic alcohol + 3 EO ether of glycolic acid, stearyl alcohol + 6 EO ether of glycolic acid; furthermore, carboxyl substituted alkylglycolic acids such as diglycolic acid, the lactic acid ether of glycolic acid, and carboxyl substituted oxaalkyl glycolic acids such as ethylene-bis-glycolic acid. Primarily, the potassium and sodium salts are employed as the alkali metal salts. The alkali metal salts of the ether carboxylic acids used as starting materials for the method according to the invention should be present if possible in dry form, since it is advisable to avoid the presence of large amounts of water during the reaction. Preferably, the reaction is conducted under substantially anhydrous conditions.

The production of the alkali metal salts of the ether carboxylic acids used as starting materials in the present method can be effected according to methods known from the literature, and is not the subject of the invention.

In order to obtain high yields, it is preferable to continuously remove the alcohol formed during the reaction from the reaction mixture.

For example, during the reaction in an autoclave under carbon dioxide pressure, this removal can be so effected that the carbon dioxide pressure is released in certain time intervals and the alcohol is constantly removed with the expelled carbon dioxide. For the complete removal of the alcohol formed, the vessel can also be briefly evacuated. However, conditions should be employed so that no air gets into the autoclave. Subsequently carbon dioxide is again forced into the autoclave by means of a compressor. The reaction can also be carried out continuously under pressure; however, with constant removal of the resulting alcohol by means of a carbon dioxide current. In order to avoid secondary reactions, a substantial excess of carbon dioxide is preferably used.

The alkali metal salts of the ether carboxylic acids are reacted according to the invention in the presence of alkali metal alcoholates with carbon dioxide under pressure. The pressure can vary within very wide limits, but should be at least 2 atmospheres gauge. The desired reaction can already be obtained with a relatively low overpressure, e.g. about 2 to 50 atmospheres. But in order to obtain good yields, it is generally desirable to utilize a carbon dioxide pressure of more than 100 atmospheres at the reaction temperature. The upper limit of the pressure is determined by the available apparatus. It can be 1000 to 2000 atmospheres or more. The pressure can be produced by corresponding pumps or compressors. In laboratory tests, liquid or solid carbon dioxide can be filled into the cooled and evacuated reaction vessel. The carbon dioxide can be recirculated, just like the other ingredients.

The reaction temperature is very critical in the present method in order to avoid decomposition of the ether carboxylic acids. In order to obtain a sufficiently rapid reaction for technical purposes, temperatures above 200°C are required. The reaction temperature, however, should not exceed 350°C if possible, unless decomposition is prevented at the same time by very high pressures. A preferred temperature range is between 250°C and 300°C. The optimum temperature depends on the desired degree of carboxylation as well as on the nature of the ether carboxylic acids used and the type of alkali metals used.

The reaction takes only a short time; but larger batches may take several hours, because of the required time for heating and cooling. Care must be taken that local overheating, which can lead to decomposition, is avoided during the heating step. For this reason, too rapid heating should be avoided. In general, a reaction time of 1 to 3 hours will be sufficient.

For carrying out the reaction, as it can be seen from the reaction equation above, at least 1 mol of alkali metal alcoholate is required for each new carboxyl group to be formed. The alkali metal alcoholate neutralizes and stabilizes at the same time the newly formed carboxyl group and prevents the metallization reaction. In some cases, a slight excess of alkali metal alcoholate is preferable. However, since the alcohol produced by the reaction should be removed, a large excess of the alkali metal alcoholate should be avoided. The alkali metal alcoholate is preferably used as an alcohol-free, finely-divided powder. In some cases it may be of advantage, for a better start to the reaction, to add to the reaction mixture a small amount of a low molecular weight aliphatic alcohol, for example, methanol or a dilower alkyl carbonate such as diethyl carbonate. Amounts of from 0 to 15% by weight, based on the weight of the reaction mixture, may be employed.

Examples of suitable alkali metal alcholates include those having 1 to 4 carbon atoms, such as alkali metal aliphatic alcoholates of 1 to 4 carbon atoms, preferably alkali metal alkanolates of 1 to 4 carbon atoms, such as sodium methylate, potassium methylate, sodium tert.-butylate, potassium tert.-butylate, particularly sodium methylate.

Water and oxygen should be excluded, as far as possible in the present method, as in all metallo-organic synthesis, if good yields are to be obtained. If necessary, water-binding substances can be added.

Furthermore, it was found advantageous to add to the reaction mixture, inert substances with a large surface area, such as kieselguhr, finely-divided silica, powdered carbon black, and finely-divided aluminum oxide, in order to improve the mechanical-physical properties of the mixture and to prevent the possible formation of lumps. The technical realization of the method is thus made considerably easier. The amount of inert additives can vary within very wide limits and is determined by the design of the apparatus used. Ordinarily, from 0 to 70% by weight, based on the weight of the reaction mixture of the finely-divided inert diluents, are employed.

Finally, the reaction can also be carried out in the presence of inert liquid diluents, such as paraffin oil. The amount of diluent is preferably so selected that a pumpable mixture is obtained. Ordinarily, from 0 to 30% by weight, based on the weight of the reaction mixture, of the inert liquid diluents are employed.

The reaction according to the invention is catalytically influenced by a number of heavy metals or heavy metal compounds. Suitable metals are, for example, iron, bismuth, zinc, nickel, copper, cadmium, titanium and chromium, which can be used as such or in the form of their oxides or salts with inorganic or organic acids, such as carbonates, bicarbonates, halides, sulfates, acetates, formates, oxalates or higher fatty acid salts. Of particular advantage for the reaction according to the invention is the use of iron or zinc powder as a catalyst.

The amount of catalyst can vary within wide limits of 0 to 15% by weight, and is preferably 0.5% to 5% by weight, based on the reaction mixture, when employed.

The method can be carried out continuously or intermittently. Thus, for example, it is possible to work according to the fluidized bed method. In an intermittent operation it is advisable to use rolling autoclaves or autoclaves equipped with a stirrer as the reaction vessels. Even in discontinuous operation it is advisable to thoroughly mix the reaction mixture, by stirring, shaking or grinding.

The reaction mixture can be worked up by dissolving the entire reaction mixture in water and filtering off the insoluble components, like the catalyst and inert additives. The ether polycarboxylic acids can be obtained from the aqueous solution by acidification with mineral acids or by treatment with a cation exchanger in acid form and subsequent working up according to the known methods.

The ether polycarboxylic acids obtained can be used with very good results as sequestering agents. In many cases, particularly for use as sequestering agents for the hardness of the water in detergents and cleaning agents, it is not neccessary to produce the ether carboxylic acids in the free acid form, since their alkali metal salts can be used with just as good results. In addition, the product mixture obtained in the method according to the invention can also be used, after they have been separated from the catalyst and inert substances.

The following examples will illustrate the invention without limiting it, however, to these examples.

EXAMPLES

In the following examples, the procedure was as follows, unless indicated otherwise. The dried anhydrous starting materials were finely ground in a ball mill and heated in a high-pressure autoclave of 500 ml capacity under carbondioxide pressure.

The "initial pressure" was the carbon dioxide pressure in the autoclave before the commencing heating. This pressure was adjusted in each case at 50°C, in view of the critical temperature of carbon dioxide. The "end pressure" was the maximum pressure observed at the corresponding reaction temperature.

In many cases, the autoclave was provided with a glass insert or partial lining. This is indicated in the respective tests.

For the working up of the reaction mixture, the crude product was dissolved in water and filtered hot. After cooling, the filtrate was mixed under stirring with a particulated cation exchange resin in acid form in order to acidify the product, whereby the carbon dioxide could escape without foaming. Subsequently, the ion-exchange resin was filtered off and the aqueous solution of the ether polycarboxylic acids was conducted through a fresh cation exchange resin column in the acid form, in order to transform it completely into the free acid. The eluate was evaporated under vacuum until dry. The total yield of ether polycarboxylic acids obtained this way corresponds to the analytical composition of the reaction mixture.

The analytical composition of the ether polycarboxylic acids obtained was determined by gas chromatography of the methyl esters after esterification of the acids with diazomethane to the methyl esters. The usual analytical data were determined from the pure single fractions obtained by distillation or gas chromatography.

In the following tables of the following examples, the individual abbreviations have the following meanings:

| | |
|---|---|
| Init. pressure | = the initial carbon dioxide pressure in atmospheres measured at 50°C. |
| E-pressure | = the end carbon dioxide pressure at the respective reaction temperature. |
| Temp. | = the reaction temp. in °C, measured in |

-continued

| | | vapor area. |
|---|---|---|
| Comp. TC% | = | the percent composition of total carboxylic acids. |
| DG | = | diglycolic acid. |
| MDG | = | methyldiglycolic acid. |
| MOA | = | methoxyacetic acid. |
| CMT | = | carboxymethyl ether of tartronic acid (2-oxa-propane-1,1,3-tricarboxylic acid). |
| DT | = | ditartronic acid (2-oxa-propane-1,1,3,3-tetracarboxylic acid). |
| OBT | = | 2-oxabutane-1,1,3-tricarboxylic acid. |
| MOM | = | methoxymalonic acid. |
| MA + B | = | malonic acid + byproducts. |
| B | = | byproducts. |

In the examples marked "x", the alcohol formed was removed after 2 hours reaction time by discharging the carbon dioxide. Subsequently, a pressure of 150 atmospheres gauge was set with fresh carbon dioxide at 250°C to 260°C, and the reaction was completed during the course of another hour at the indicated temperature.

EXAMPLES 1 to 3 (glass insert)

Batch: 17.8 gm of disodium salt of diglycolic acid (0.1 mol)
8.1 gm of sodium methylate powder (0.15 mol)
4.0 gm of Aerosil
Heating time: 3 hours to reaction temperature The results of the rests are compiled in Table I below.

TABLE I

| Example | Init. Pressure | End Pressure | Temp. °C | Comp. TC% |
|---|---|---|---|---|
| 1 | 240 | 850 | 270 | 70.4 DG;27.3 CMT; 0.4 DT 1.9 MA+B |
| 2ˣ | 240 | 960/2h 150–200/1h | 270 | 62.7 DG;33.7 CMT; 3.6 MA+B |
| 3ˣ + 5 ml methanol | 240 | 840/2h 150–160/1h | 270 | 61.6 DG;35.4 35.4 CMT; 3.0 MA+B |

EXAMPLE 4 to 6

Batch: 17.8 gm of dipotassium salt of diglycolic acid (0.085 mol)
8.1 gm of sodium methylate powder (0.15 mol)
4.0 gm of Aerosil
Heating time: 3 hours at reaction temperature.

The test results are compiled in Table II below.

TABLE II

| Ex. | Init. Pressure | End Pressure | Temp. °C | Comp. TC% |
|---|---|---|---|---|
| 4ˣ | 240 | 680/2h 150–170/1h | 270 | 52.8 DG;38.0 CMT;2.9DT; 6.2 MA+B |
| 5ˣ | 120 | 350/2h 150–200/1h | 270 | 59.2 DG;32.7 CMT;2.7DT; 5.4 MA+B |
| 6ˣ | 240 | 1000/2h 200/1h | 270 | 0.2 DG;77.3 CMT; 19.4 DT; 3.1 MA+B |

EXAMPLES 7 to 8 (glass insert)

Batch: 21.0 gm of dipotassium salt of diglycolic acid (0.1 mol)
8.1 gm of sodium methylate (0.15 mol)
4.0 gm of Aerosil
1.0 gm of iron powder as catalyst
Heating time: 3 hours at reaction temperature.

The results of the tests are compiled in Table III below.

TABLE III

| Ex. | Init. Pressure | End Pressure | Temp. °C | Comp. TC% |
|---|---|---|---|---|
| 7ˣ | 270 | 900/2h 160/1h | 270 | 54.9 DG;35.5 CMT;1.4 DT 7.8 MA+B |
| 8 | 240 | 880 | 270 | 59.4 DG;32.8 CMT; 2.8 DT 5.0 MA+B |

EXAMPLES 9 to 10 (glass insert)

Batch: 21.0 gm of dipotassium salt of diglycolic acid (0.1 mol)
10.5 gm of potassium methylate (0.15 mol)
4.0 gm of Aerosil
Heating Time: 3 hours at reaction temperature The results of the tests are compiled in Table IV below.

TABLE IV

| Ex. | Init. Pressure | End Pressure | Temp. °C | Comp. TC% |
|---|---|---|---|---|
| 9ˣ | 260 | 710/2h 160/1h | 270 | 27.5 DG;50.4 CMT;12.8 DT 9.3 MA+B |
| 10ˣ | 250 | 750/2h 150/1h | 250 | 38.9 DG;49.7 CMT;7.1 DT; 4.3 MA+B |

EXAMPLE 11

Batch: 21.0 gm of dipotassium salt of diglycolic acid (0.1 mol)
17.7 gm of potassium tert.-butylate (95%) (0.15 mol)
4.0 gm of Aerosil
Heating time: 3 hours at reaction temperature The test results are compiled in Table V below.

TABLE V

| Ex. | Init. Pressure | End Pressure | Temp. °C | Comp. TC% |
|---|---|---|---|---|
| 11ˣ | 270 | 850/2h 160/1h | 270 | 43.8 DG;42.7 CMT;6.0 DT; 6.5 MA+B |

EXAMPLE 12 (glass insert)

Batch: 17.8 gm of disodium salt of diglycolic acid (0.1 mol)
8.1 gm of sodium methylate (0.15 mol)
4.0 gm of Aerosil
5.0 ml of diethyl carbonate
Heating time: 3 hours at reaction temperature The test results are compiled in Table VI below.

TABLE VI

| Example | Init. Pressure | End Pressure | Temp. °C | Comp. TC% |
|---|---|---|---|---|
| 12ˣ | 240 | 820/2h 170/1h | 270 | 60.6 DG;34.7 CMT; 4.7 MA+B |

EXAMPLE 13 (Glass Insert)

Batch: 17.8 gm of dipotassium salt of diglycolic acid (0.085 mol)
8.1 gm of sodium methylate (0.15 mol) dissolved in methanol
4.0 gm of Aerosil The dipotassium salt of diglycolic acid was mixed with 27 gm of a 30% sodium methylate solution. Subsequently, the methanol was distilled off in vacuum; and the salt mixture obtained was ground together with the Aerosil in a ball mill. The test results are compiled in Table VII below.

TABLE VII

| Example | Init. Pressure | End Pressure | Temp. °C | Comp. TC% |
|---|---|---|---|---|
| 13* | 270 | 875/2h | 270 | 46.1 DG;43.7 CMT; |
| | | 200/1h | 270 | 4.4 DT;5.8 MA+B |

EXAMPLE 14

Batch: 10.5 gm of dipotassium salt of diglycolic acid (0.05 mol)
25.0 gm of quartz sand (sea sand)
4.05 gm of sodium methylate (0.075 mol)

The mixture was ground for 12 hours in a ball mill. The test results are compiled in Table VIII below.

TABLE VIII

| Example | Init. Pressure | End Pressure | Temp. °C | Comp. TC% |
|---|---|---|---|---|
| 14* | 270 | 940/2h | 270 | 43.5 DG;46.4 CMT; |
| | | 190/1h | 270 | 4.1 DT;6.0 MA+B |

EXAMPLE 15

Batch: 21.0 gm of dipotassium salt of diglycolic acid (0.1 mol)
8.1 gm of sodium ethylate (0.15 mol)
6.0 gm of Aerosil The mixture of the dipotassium salt of diglycolic acid and sodium methylate was ground for 24 hours in a ball mill. After the addition of Aerosil, the mixture was ground for another 30 minutes. The tests results are compiled in Table IX below.

TABLE IX

| Example | Init. Pressure | End Pressure | Temp. °C | Comp. TC% |
|---|---|---|---|---|
| 15* | 270 | 840/2h | 270 | 45.7 DG;42.0 CMT; |
| | | 175/1h | 270 | 3.7 DT;8.6 MA+B |

EXAMPLE 16

Batch: 21.0 gm of dipotassium salt of diglycolic acid (0.1 mol)
8.1 gm of sodium methylate (0.15 mol)

The test results are compiled in Table X below.

TABLE X

| Example | Init. Pressure | End Pressure | Temp. °C | Comp. TC% |
|---|---|---|---|---|
| 16* | 270 | 950/2h | 270 | 61.7 DG;22.7 CMT; |
| | | 170/1h | 270 | 0.8 DT;14.8 MA+B |

EXAMPLE 17

Batch: 12.8 gm of potassium salt of methoxy-acetic acid (0.1 mol)
8.1 gm of sodium methylate
4.0 gm of Aerosil The results of the tests are compiled in Table XI below.

TABLE XI

| Example | Init. Pressure | End Pressure | Temp. °C | Comp. TC% |
|---|---|---|---|---|
| 17* | 270 | 880/2h | 270 | 18.8 MOM;70.2 MOA; |
| | | 200/1h | 270 | 11.6 B |

EXAMPLE 18

Batch: 23.5 gm of dipotassium salt of methyl-diglycolic acid (0.1 mol)
10.5 gm of potassium methylate (0.15 mol)
4.0 gm of Aerosil The results of the tests are compiled in Table XII below.

TABLE XII

| Example | Init. Pressure | End Pressure | Temp °C | Comp. TC% |
|---|---|---|---|---|
| 18* | 270 | 890/2h | 270 | 66.2 MDG; 26.2 OBT |
| | | 180/1h | 270 | 7.6 B |

Although the present invention has been disclosed in connection with a few preferred embodiments thereof, variations and modifications may be restored to by those skilled in the art without departing from the principles of the new invention. All of these variations and modifications are considered to be within the true spirit and scope of the present invention as disclosed in the foregoing description and defined by the appended claims.

We claim:
1. A process for the production of ether polycarboxylic acids consisting essentially of reacting an alkali metal salt of an ether carboxylic acid having the formula

R — O — CHR' — COOH wherein R is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and R' is a member selected from the group consisting of hydrogen and alkyl having from 1 to 4 carbon atoms with an excess of carbon dioxide in the presence of (1) at least an equimolar amount of an alkali metal alcoholate of an alkanol having 1 to 4 carbon atoms and (2) from 0% to 70% by weight, based on the weight of the reaction mixture of a heavy metal catalyst, an alkanol having 1 to 4 carbon atoms, a dialkyl carbonate having 1 to 4 carbon atoms in the alkyl, a finely-divided inert diluent and an inert liquid diluent, at a temperature of between 200°C and 350°C under a pressure of at least 2 atmospheres gauge, for a time sufficient to effect carboxylation, and recovering said ether polycarboxylic acids.

2. The process of claim 1, wherein said temperature is between 250°C and 300°C.

3. The process of claim 1, wherein said alkali metal alcoholate is sodium alcoholate.

4. The process of claim 1, wherein said alkali metal alcoholate is sodium methylate.

5. The method of claim 1, wherin said reaction is conducted under substantially anhydrous conditions in the substantial absence of oxygen.

6. The process of claim 1, wherein the alcohol formed during the reaction is removed intermittently from the reaction mixture.

7. The process of claim 1, wherein from 0.5% to 15% by weight of the total mixture of a substance selected from the group consisting of an alkanol having 1 to 4 carbon atoms and diethyl carbonate is added to the reaction mixture.

8. The process of claim 1, wherein said ether polycarboxylic acid is carboxymethyl tartronic acid and wherein said ether carboxylic acid is diglycolic acid.

9. The process of claim 1, wherein from 0.5% to 5% by weight of iron powder is employed as a heavy metal catalyst.

10. The process of claim 1, wherein from 0.5% to 5% by weight of zinc powder is employed as a heavy metal catalyst.

* * * * *